(12) United States Patent
Kakiuchi et al.

(10) Patent No.: US 8,212,048 B2
(45) Date of Patent: Jul. 3, 2012

(54) METHOD OF PRODUCING AROMATIC COMPOUND

(75) Inventors: Fumitoshi Kakiuchi, Yokohama (JP); Yusuke Matsuura, Funabashi (JP); Masato Ueda, Tsukuba (JP)

(73) Assignees: Sumitomo Chemical Company, Limited, Tokyo (JP); Osaka University, Osaka (JP)

( * ) Notice: Subject to any disclaimer, the term of this patent is extended or adjusted under 35 U.S.C. 154(b) by 921 days.

(21) Appl. No.: 12/162,549

(22) PCT Filed: Feb. 2, 2007

(86) PCT No.: PCT/JP2007/052304
§ 371 (c)(1),
(2), (4) Date: Sep. 25, 2008

(87) PCT Pub. No.: WO2007/089044
PCT Pub. Date: Aug. 9, 2007

(65) Prior Publication Data
US 2009/0043096 A1    Feb. 12, 2009

(30) Foreign Application Priority Data

Feb. 3, 2006    (JP) .................................. 2006-026697

(51) Int. Cl.
C07D 401/04 (2006.01)
C07D 403/04 (2006.01)
C07D 213/02 (2006.01)
C07D 213/22 (2006.01)
C07D 213/127 (2006.01)
C07D 215/00 (2006.01)
C07D 221/10 (2006.01)
C07D 237/06 (2006.01)
C07D 237/30 (2006.01)
C07D 239/24 (2006.01)
C07D 239/70 (2006.01)
C07D 241/10 (2006.01)
C07D 241/36 (2006.01)
C07D 251/12 (2006.01)
C07D 277/20 (2006.01)
C07D 275/02 (2006.01)
C07D 261/06 (2006.01)
C07D 263/30 (2006.01)
C07D 233/54 (2006.01)
C07D 231/10 (2006.01)
C07D 231/12 (2006.01)
C07D 333/10 (2006.01)

(52) U.S. Cl. ..................... 546/342; 546/112; 546/268.1; 546/269.7; 546/271.1; 546/271.4; 546/272.7; 546/275.4; 544/180; 544/224; 544/238; 544/242; 544/336; 548/146; 548/206; 548/215; 548/240; 548/250; 548/300.1; 548/356.1; 549/29

(58) Field of Classification Search ................... 546/342, 546/112, 268.1, 268.4, 269.7, 271.1, 272.1, 546/273.7, 275.4; 544/180, 224, 238, 242, 544/336; 548/146, 206, 215, 240, 300.1, 548/356.1; 549/29
See application file for complete search history.

(56) References Cited

U.S. PATENT DOCUMENTS

| 5,530,157 A | 6/1996 | Mewshaw et al. |
| 2002/0006952 A1 | 1/2002 | Reich et al. |
| 2004/0106627 A1 | 6/2004 | Gardelli et al. |

FOREIGN PATENT DOCUMENTS

| JP | 2004-501083 A | 1/2004 |
| JP | 2004-504304 A | 2/2004 |

OTHER PUBLICATIONS

Lim, Y. G. et al., Rhodium (I)—catalyzed ortho-alkenylation of 2-phenylpyridines with alkynes, Tetrahedron Letters, (2001), vol. 42, No. 43, pp. 7609-7612.
Oi, Shuichi et al., Ruthenium complex-catalyzed direct ortho arylation and alkenylation of 2-arylpyridines with organic halides, Organic Letters, (2001), vol. 3, No. 16, pp. 2579-2581.
Oi, Shuichi et al., Ortho-selective direct cross-coupling reaction of 2-aryloxazolines and 2-arylimidazolines with aryl and alkenyl halides catalyzed by ruthenium complexes, Journal of Organic Chemistry, (2005), vol. 70, No. 8, pp. 3113-3119.
Gomes, Paulo et al., Cobalt-catalyzed electrochemical vinylation of aryl halides using vinylic acetates, Tetrahedron, (2003), vol. 59, No. 17, pp. 2999-3002.
Lal, Bansi et al., A novel base-catalyzed carbon-nitrogen bond fission in some heterocycles, Journal of Organic Chemistry, (1990), vol. 55, No. 17, pp. 5117-5124.
86th Annual Meeting of The Chemical Society of Japan, Mar. 28, 2005, Abstract H2-43.
86th Annual Meeting of the Chemical Society of Japan, Mar. 28, 2006, Abstract H2-43.

*Primary Examiner* — Venkataraman Balasubramanian
(74) *Attorney, Agent, or Firm* — Sughrue Mion, PLLC

(57) ABSTRACT

A method of producing an aromatic compound of the following formula (3) comprising reacting a compound of the following formula (1) with an olefin compound of the following formula (2) in the presence of a transition metal complex:

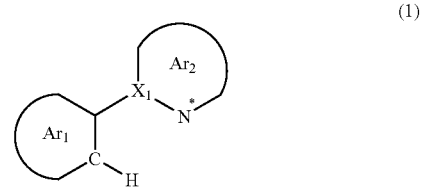

(1)

(wherein, an $Ar_1$ ring represents an aromatic hydrocarbon ring or aromatic heterocyclic ring, an $Ar_2$ ring represents a heterocyclic ring containing $X_1$ and $N^*$, and the $X_1$ represents a nitrogen atom or carbon atom and the N represents a nitrogen atom connecting via a double bond to either one of two adjacent atoms in the $Ar_2$ ring.)

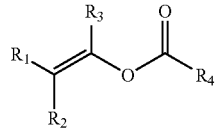
(2)
(wherein, $R_1$, $R_2$, $R_3$ and $R_4$ represent each independently a hydrogen atom, an alkyl group having 1 to 10 carbon atoms or an aryl group having 6 to 18 carbon atoms.)
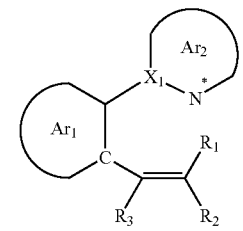
(3)
(wherein, $Ar_1$, $Ar_2$, $X_1$, $N^*$, $R_1$, $R_2$ and $R_3$ represent the same meanings as described above.).
13 Claims, No Drawings

METHOD OF PRODUCING AROMATIC COMPOUND

TECHNICAL FIELD

The present invention relates to a method of producing an aromatic compound.

BACKGROUND ART

Aromatic compounds are useful as raw materials for production of electronic materials, medicines, agricultural chemicals, industrial chemicals and the like, and development of new production methods thereof is desired.

As a method of producing an aromatic compound having a 2-pyridyl group which is a nitrogen-containing heterocyclic ring, and an alkenyl group at adjacent positions of a benzene ring, there is reported a method as described below of reacting a compound having a 2-pyridyl group on a benzene ring with a brominated olefin compound as an alkenylating agent in the presence of a ruthenium complex (Organic Letters 2001, Vol. 3, No. 16, p. 2579-2581).

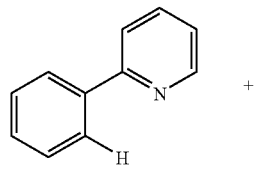

The above-described method, however, is not satisfactory from the ecological standpoint owing to use of a bromide as an alkenylating agent, thus, a production method which is improved in this point has been desired.

DISCLOSURE OF THE INVENTION

An object of the present invention is to provide a novel method of producing a compound having a nitrogen-containing heterocyclic ring and an alkenyl group at adjacent positions of an aromatic ring in which an olefin compound containing no halogen is used as an alkenylating agent.

The present invention provides a method of producing an aromatic compound of the following formula (3) comprising reacting a compound of the following formula (1) with an olefin compound of the following formula (2) in the presence of a transition metal complex:

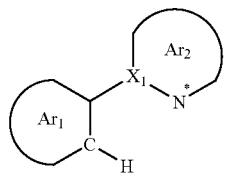

(wherein, an $Ar_1$ ring represents an aromatic hydrocarbon ring or aromatic heterocyclic ring, an $Ar_2$ ring represents a heterocyclic ring containing $X_1$ and N*, and the $X_1$ represents a nitrogen atom or carbon atom and the N* represents a nitrogen atom connecting via a double bond to either one of two adjacent atoms in the ring structure. The $Ar_1$ ring and/or the $Ar_2$ ring may optionally have a group selected from an alkyl group having 1 to 10 carbon atoms, an alkoxy group having 1 to 10 carbon atoms, an aryl group having 6 to 18 carbon atoms and an aryloxy group having 6 to 10 carbon atoms. The $Ar_1$ ring and the $Ar_2$ ring may be further connected directly or via a divalent group.)

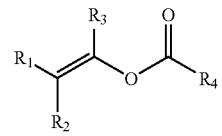

(wherein, $R_1$, $R_2$, $R_3$ and $R_4$ represent each independently a hydrogen atom, an alkyl group having 1 to 10 carbon atoms or an aryl group having 6 to 18 carbon atoms.)

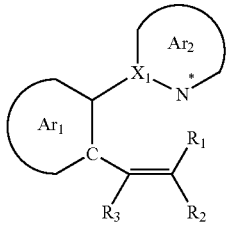

(wherein, $Ar_1$, $Ar_2$, $X_1$, N*, $R_1$, $R_2$ and $R_3$ represent the same meanings as described above.).

Further, the present invention relates to a method of producing an aromatic compound of the following formula (4) comprising reacting a compound of the formula (1') with an olefin compound of the above-described formula (2) in the presence of a transition metal complex:

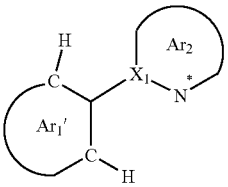

(wherein, an $Ar_1'$ ring represents an aromatic hydrocarbon ring or aromatic heterocyclic ring, an $Ar_2$ ring, $X_1$ and N* represent the same meanings as described above, and the $Ar_1'$ ring and/or the $Ar_2$ ring may optionally have a group selected from an alkyl group having 1 to 10 carbon atoms, an alkoxy group having 1 to 10 carbon atoms, an aryl group having 6 to 18 carbon atoms and an aryloxy group having 6 to 10 carbon atoms, and the $Ar_1'$ ring and the $Ar_2$ ring may be further connected directly or via a divalent group.)

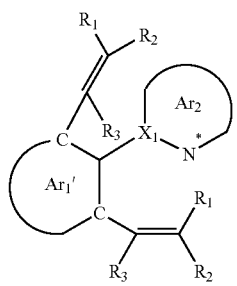

(4)

(wherein, $Ar_1'$, $Ar_2$, $X_1$, $N^*$, $R_1$, $R_2$ and $R_3$ represent the same meanings as described above.).

MODE FOR CARRYING OUT THE INVENTION

The $Ar_1$ ring in an aromatic compound of the formula (1) represents an aromatic hydrocarbon ring or aromatic heterocyclic ring. The $Ar_1$ ring has a hydrogen atom connected to one or two carbon atoms at a position bonding to the $Ar_2$ ring.

In the case of alkenylation using a compound of the above-described formula (1') having hydrogen atoms connected to two carbon atoms at a position, a compound of the above-described formula (4) having two alkenyl groups derived from an olefin compound of the above-described formula (2) can be produced as a product.

Also, a compound of the following formula (3') having one alkenyl group derived from an olefin compound of the above-described formula (2) can be produced.

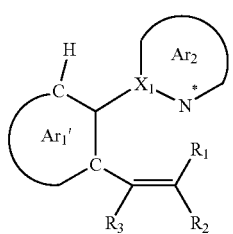

(3')

Examples of the aromatic hydrocarbon rings $Ar_1$ and $Ar_1'$ include a benzene ring, naphthalene ring, anthracene ring, phenanthrene ring, pyrene ring, fluorene ring and the like, and examples of the aromatic heterocyclic rings $Ar_1$ and $Ar_1'$ include a furan ring, oxazole ring, isooxazole ring, thiophene ring, thiazole ring, isothiazole ring, pyrrole ring, imidazole ring, pyrazole ring, tetrazole ring, pyridine ring, pyrazine ring, pyrimidine ring, pyridazine ring, triazine ring, indole ring, indazole ring, quinoline ring, isoquinoline ring, purine ring, naphthyridine ring, phthalazine ring, quinoxaline ring, quinazoline ring, carbazole ring, phenanthridine ring, phenanthroline ring, acridine ring, phenazine ring and the like.

The $Ar_2$ ring represents a heterocyclic ring containing $X_1$ and $N^*$, and the $X_1$ represents a nitrogen atom or carbon atom and the N represents a nitrogen atom connecting via a double bond to one of two adjacent atoms of the nitrogen in the $Ar_2$ ring.

Examples of the $Ar_2$ ring include aromatic heterocyclic rings such as an imidazole ring, pyrazole ring, tetrazole ring, oxazole ring, isooxazole ring, thiazole ring, isothiazole ring, pyridine ring, pyrazine ring, pyrimidine ring, pyridazine ring, triazine ring, indole ring, indazole ring, quinoline ring, isoquinoline ring, purine ring, naphthyridine ring, phthalazine ring, quinoxaline ring, quinazoline ring, carbazole ring, phenanthridine ring, phenanthroline ring, acridine ring, phenazine ring and the like, and non-aromatic heterocyclic rings such as an oxazoline ring, thiazoline ring, pyrazoline ring and the like.

Also, the $Ar_1$ ring or $Ar_1'$ ring and the $Ar_2$ ring can further be connected directly or via a divalent group. Here, the divalent group includes —CRxRw-, —O—, —S—, —SO—, —$SO_2$—, —NRx-, —SiRxRw-, —PRx-, —P(=O)Rx-, —BRx-, —$(CRxRw)_2$-, —CRxRw-O—, —CRxRw-S—, —CRxRw-NRx-, —C(=O)—O—, —C(=O)—NH—, —$(CRxRw)_3$-, —$(CRxRw)_4$-, —CRx=N—, —(CRx=CRw)-, phenylene, naphthylene and the like.

Examples of the condensed ring to be formed by connecting the $Ar_1$ ring and the $Ar_2$ ring include benzo[h][1,6]naphthyridine, thieno[2,3-h]quinoline, furo[2,3-h]quinoline, 7H-pyrrolo[2,3-h]quinoline, 3H-9-aza-cyclopenta[a]naphthalene, 7H-pyrrolo[3,4-h]quinoline and the like.

Here, Rx and Rw represent each independently a hydrogen atom, an alkyl group having 1 to 10 carbon atoms, an alkoxy group having 1 to 10 carbon atoms, an aryl group having 6 to 18 carbon atoms or an aryloxy group having 6 to 18 carbon atoms.

The $Ar_1$ ring, $Ar_1'$ ring and/or the $Ar_2$ ring optionally have a group selected from an alkyl group having 1 to 10 carbon atoms, an alkoxy group having 1 to 10 carbon atoms, an aryl group having 6 to 18 carbon atoms and an aryloxy group having 6 to 18 carbon atoms.

Examples of the alkyl group having 1 to 10 carbon atoms include methyl, ethyl, n-propyl, isopropyl, n-butyl, sec-butyl, tert-butyl, isobutyl, n-pentyl, 2,2-dimethylpropyl, cyclopentyl, n-hexyl, cyclohexyl, 2-methylpentyl, 2-ethylhexyl and the like, and hydrogen in these alkyl groups may optionally be substituted by a halogen such as fluorine and the like, and for example, trifluoromethyl is mentioned.

Examples of the alkoxy group having 1 to 10 carbon atoms include methoxy, ethoxy, n-propyloxy, isopropyloxy, n-butyloxy, sec-butyloxy, tert-butyloxy, isobutyloxy, n-pentyloxy, 2,2-dimethylpropyloxy, cyclopentyloxy, n-hexyloxy, cyclohexyloxy, 2-methylpentyloxy, 2-ethylhexyloxy and the like.

Examples of the aryl group having 6 to 18 carbon atoms include phenyl, naphthyl, anthracenyl, phenanthryl, pyrenyl and the like.

Examples of the aryloxy group having 6 to 18 carbon atoms include phenoxy, naphthyloxy, anthracenyloxy, phenanthryloxy, pyrenyloxy and the like.

Specific examples of the compound of the above-described formula (1) or formula (1') include 2-phenylpyridine, 2-o-tolylpyridine, 2-o-tolyl-3-methylpyridine, 2-o-tolyl-4-methylpyridine, 7,8-benzoquinoline, 2-(2-methoxyphenyl)-pyridine, 2-(3-methoxyphenyl)-pyridine, 2-(3-methylphenyl)-pyridine, 2-(3-trifluoromethylphenyl)-pyridine, 2-o-tolyl-4,4-dimethyloxazoline, 3-phenyl-2-N-methyl-1,2,4,5-tetrazole, 2-phenyl-1-N-methylimidazole, 1-N-phenylpyrazole, 2-methyl-4-phenylthiazole, 2-(3-thienyl)-pyridine, 2-(3-furyl)-pyridine, 2-(3-pyrrolyl)-pyridine and the like.

$R_1$, $R_2$, $R_3$ and $R_4$ in the olefin compound of the above-described formula (2) to be used in the present invention represent each independently a hydrogen atom, an alkyl group having 1 to 10 carbon atoms or an aryl group having 6 to 18 carbon atoms.

Examples of the alkyl group having 1 to 10 carbon atoms include methyl, ethyl, n-propyl, isopropyl, n-butyl, sec-butyl, tert-butyl, isobutyl, n-pentyl, 2,2-dimethylpropyl, cyclopentyl, n-hexyl, cyclohexyl, 2-methylpentyl, 2-ethylhexyl and the like.

Examples of the aryl group having 6 to 18 carbon atoms include phenyl, naphthyl, anthracenyl, phenanthryl, pyrenyl and the like.

Specific examples of the olefin compound of the formula (2) include vinyl acetate, vinyl pivalate, vinyl butyrate, vinyl benzoate, β-acetyloxystyrene and the like.

The using amount of the olefin compound of the formula (2) is usually 0.5 mol or more, preferably 1.0 mol or more and preferably 1.5 mol or more with respect to 1 mol of the compound of the formula (1) or formula (1') as another raw material. The upper limit of the using amount of the olefin compound is usually preferably 15 mol or less and more preferably 8 mol or less.

The reaction is preferably carried out at the reaction temperature in a range of −50° C. to 300° C. and at the reaction time in a range of 0.5 hour to 200 hours.

Specific examples of the compound of the formula (3) or (3') to be obtained as a product include 2-(2-vinylphenyl)pyridine, 2-(2-vinyl-6-methylphenyl)pyridine, 2-(2-vinyl-6-methylphenyl)-3-methylpyridine, 2-(2-vinyl-6-methylphenyl)-4-methylpyridine, 10-(β-styryl)benzo[h]quinoline, 2-(2-methoxy-6-vinylphenyl)-pyridine, 2-(3-methoxy-6-vinylphenyl)-pyridine, 2-(3-methyl-6-vinylphenyl)-pyridine, 2-(3-trifluoromethyl-6-vinylphenyl)-pyridine, 2-(2-vinyl-6-methylphenyl)-4,4-dimethyloxazoline, 3-(2-styrylphenyl)-2-N-methyl-1,2,4,5-tetrazole, 2-(2-vinylphenyl)-1-N-methylimidazole, 1-N-(2-vinylphenyl)pyrazole, 2-methyl-4-(2-vinylphenyl)thiazole, 2-(2-vinylthiophen-3-yl)-pyridine, 2-(2-styrylthiophen-3-yl)-pyridine, 2-(2-vinylfuran-3-yl)-pyridine, 2-(2-vinylpyrrol-3-yl)-pyridine and the like.

Examples of the compound of the above-described formula (4) include 2-(2,6-divinylphenyl)pyridine, 1-(2,6-distyrylphenyl)-1H-pyrazole, 2-(2,6-distyrylphenyl)-pyridine and the like.

Regarding the reaction conditions, the using amount of an olefin compound of the formula (2) is preferably 0.5 mol to 8 mol with respect to 1 mol of a compound of the formula (1) as another raw material, and the reaction is preferably carried out at the reaction temperature in a range of 50° C. to 130° C. and at the reaction time in a range of 0.5 hour to 200 hours.

As described above, when a compound of the formula (1') is used as a raw material, both a compound of the above-described formula (3') and a compound of the above-described formula (4) can be usually produced, depending on the structure of the formula (1') and the structure (steric structure, electronic structure owing to the presence of an electron withdrawing group and the like) of a compound of the formula (2) to be used as a raw material.

In general, for improving the selectivity of production of a compound of the above-described formula (3'), it is preferable that the using amount of an olefin compound of the formula (2) is preferably 0.5 mol to 4 mol, more preferably 0.5 mol or more and 3 mol or less with respect to 1 mol of a compound of the formula (1') as another raw material in the reaction.

For improving the selectivity of production of a compound of the above-described formula (4), it is preferable that the using amount of a compound of the formula (2) is 4 mol or more, more preferably 5 mol or more and 8 mol or less with respect to 1 mol of a compound of the formula (1') as another raw material in the reaction.

The transition metal complex to be used in the production method of the present invention is preferably at least one selected from ruthenium complexes and rhodium complexes, and examples thereof include $Ru_3(CO)_{12}$ (rutheniumcarbonyl), $Rh_4(CO)_{12}$ (tetrarhodiumdodecacarbonyl), $RhCl(PPh_3)_3$ (chlorotris(triphenylphosphine)rhodium(I)), $[RhCl(coe)_2]_2$ (chlorobis(cyclooctene)rhodium(II) dimer), Ru(cod)(cot) ((cyclooctadiene)(cyclooctatriene)ruthenium), $Ru(CO)_3(PPh_3)_2$ (tricarbonylbis(triphenylphosphine)ruthenium) and the like. Preferably, Ru(cod)(cot), $[RhCl(coe)_2]_2$ and $Rh_4(CO)_{12}$ are used, and of them, Ru(cod)(cot) is particularly preferable.

The using amount of these complexes is about 0.01 mol % or more and 50 mol % or less, preferably about 1.0 mol % or more and 20 mol % or less, further preferably about 3 mol % or more and 15 mol % or less with respect to an aromatic compound of the formula (1) as a raw material.

The production method of the present invention is preferably carried out in the presence of a solvent. In this case, the solvent to be used is not particularly restricted, and the production method can be carried out using a solvent inert to this reaction, and examples thereof include toluene, DMF (dimethylformamide), NMP (1-methyl-2-pyrrolidinone), THF (tetrahydrofuran), dioxane, isopropanol, acetonitrile, pinacolone and the like. Preferably, toluene, NMP and dioxane are listed.

The using amount of the solvent is not particularly restricted, and used in an amount of 1-fold or more and 100-fold or less with respect to the weight of a compound of the formula (1). Preferably, it is used in an amount of 2-fold or more and 30-fold or less.

Usually, this reaction is carried out under an atmosphere of an inert gas such as nitrogen, argon and the like.

Though the reaction time is not particularly restricted, for example, time when one of raw materials exhausted can be regarded as terminal, or time when the amount of a product reaches the maximum amount or constant amount can be regarded as terminal, and the like. The reaction usually terminates in 0.5 hour to 200 hours.

The reaction temperature is in a range of usually about −50° C. to 300° C., preferably about 50° C. to 130° C.

In this reaction, phosphines such as triphenylphosphine, tri-2-furylphosphine, 1,3-bisdiphenylphosphinopropane and the like, and olefins such as norbornadiene, dimethyl phthalate and the like, can also be added.

In this reaction, for example, bases such as potassium carbonate, potassium tert-butoxide, cesium carbonate, triethylamine, 2,6-lutidine, sodium acetate, pyridine and the like can also be added.

In this reaction, for example, proton sources such as benzoic acid, formic acid, acetic acid and the like may also be added.

The reaction vessel to be used in this synthesis reaction may be dried or may not be dried, and preferably, the reaction is carried out using a dried vessel. As an operation, the whole reaction apparatus is purged with an inert gas such as nitrogen, argon and the like. Into this vessel, a transition metal complex, a compound of the formula (1), an olefin compound of the formula (2), and if necessary, a solvent, are charged, and mixed with stirring. This mixture is reacted, if necessary, while stirring under reflux with heating.

After completion of the reaction, an desired aromatic compound of the formula (3) can be obtained, for example, by condensing the resultant reaction mixture as it is, or by pouring the reaction mixture into water, carrying out an extraction treatment using an organic solvent such as toluene, ethyl acetate, diethyl ether, dichloromethane and the like and condensing the resultant organic layer. If necessary, column chromatography, extraction, re-crystallization, distillation and the like can be effected for purification.

One of aromatic compounds of the present invention is an aromatic compound wherein an $Ar_1$ ring or $Ar_1'$ ring in the above-described formulae (3) and (4) is an aromatic heterocyclic ring containing a heteroatom in the ring structure, and preferable are aromatic heterocyclic rings containing 1 to 3 heteroatoms in the ring structure. The heteroatom includes oxygen, nitrogen, sulfur and the like.

Specifically mentioned as the aromatic heterocyclic ring are a furane ring, oxazole ring, isooxazole ring, thiophene ring, thiazole ring, isothiazole ring, pyrrole ring, imidazole ring, pyrazole ring, tetrazole ring, pyridine ring, pyrazine ring, pyrimidine ring, pyridazine ring, triazine ring, indole ring, indazole ring, quinoline ring, isoquinoline ring, purine ring, naphthyridine ring, phthalazine ring, quinoxaline ring, quinazoline ring, carbazole ring, phenanthridine ring, phenanthroline ring, acridine ring, phenazine ring and the like, and preferable are a furane ring, pyrrole ring, thiophene ring, pyridine ring and the like.

Specific examples of the aromatic compound of the present invention include 2-(2-vinylthiophen-3-yl)-pyridine, 2-(2-styrylthiophen-3-yl)-pyridine, 2-(2-vinylfuran-3-yl)-pyridine, 2-(2-vinylpyrrol-3-yl)-pyridine, 2-(3-vinylpyrazine-2-yl)-pyridine, 2-(5-vinylthiazole-4-yl)-pyridine, 2-(5-vinyloxazol-4-yl)-pyridine, 2-(5-vinyl[1,2,4]triazin-6-yl)-pyridine and the like.

The present invention will be illustrated further in detail by examples below, but the present invention is not limited to them.

EXAMPLE 1

Production of 2-[2-methyl-6-(2-methyl-propenyl)-phenyl]-pyridine

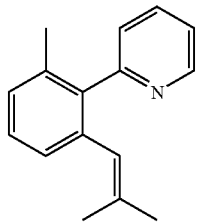

A Teflon (registered trade mark)-coated magnetic stirring rod was placed in a 4 mL pressure proof screw vial, dried with heating, then, $N_2$ gas was allowed to flow through the reaction apparatus for several minutes to purge the whole reaction apparatus with nitrogen. The reaction vessel was left to cool to room temperature, then, under a nitrogen flow, into the reaction vessel was added Ru(cod)(cot) complex (0.1 mmol, 31.6 mg), trisfurylphosphine (0.1 mmol, 23.2 mg), 2-o-tolylpyridine (1 mmol, 169 mg), 2-methylpropenyl acetate (3 mmol, 342.4 mg) and toluene (1 mL), and the reaction vessel was sealed. The mixture was heated at 100° C. by an oil bath, and reacted for 24 hours. 50 hours after, the reaction solution was left to cool to room temperature, then, an internal standard was added, and the product was quantified by gas chromatography. Isolation of the product was carried out by silica gel column chromatography (i.d.=30 mm; length=170-250 mm; hexane:EtOAc:$Et_3$N=8:1:0.1; 25 mL each).

A subject substance 2-[2-methyl-6-(2-methyl-propenyl)-phenyl]-pyridine was obtained with a yield of 86%.

IR (neat) 3058 m, 2969 m, 2856 m, 1654 w, 1587 s, 1563 m, 1459 s, 1421 m, 1376 m, 1280 w, 1182 w, 1147 w, 1091 w, 1064 w, 1025 w, 987 w, 892 m, 840 m, 775 m, 752 s, 649 m, 622 m, 472 s, 441 s, cm$^{-1}$ $^1$H NMR (CDCl$_3$) d 1.658 (d, J=1.4 Hz, 3 H, CH$_3$), 1.719 (dt, J=1.4 Hz, 3 H, CH$_3$), 2.083 (s, 3 H, CH$_3$), 5.802 (s, 1 H, CH), 7.11-7.28 (m, 5 H, ArH), 7.700 (td, J=7.6 Hz, 1.9 Hz, 1 H, ArH), 8.692 (dd, J=4.9 Hz, 1.9 Hz, 1 H, ArH);

$^{13}$C NMR (CDCl$_3$) d 19.41, 20.21, 26.09, 121.42, 124.33, 125.18, 127.23, 127.37, 128.12, 134.93, 135.76, 135.91, 137.15, 139.81, 149.19, 159.64;

MS m/z (% relative intensity) 223 (M$^+$, 5), 209 (17), 208 (100), 90 (10), 51 (10)

Elemental Analysis Anal. Calcd for C$_{16}$H$_{17}$N: C, 86.05; H, 7.67; N, 6.27%. Found: C, 85.93; H, 7.38; N, 6.38%.

EXAMPLE 2

Production of 1-(2-styrylphenyl)-1H-pyrazole

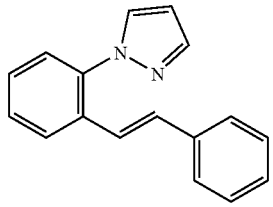

A Teflon-coated magnetic stirring rod was placed in a 10 mL two-necked flask which was then equipped with a reflux condenser. The reflux condenser was connected to a pressure reduced/nitrogen line, and the whole apparatus was dried with heating under reduced pressure. Thereafter, N$_2$ gas was charged in the reaction apparatus and the whole reaction apparatus was purged with nitrogen. The reaction vessel was left to cool to room temperature, then, Ru(cod)(cot) complex (0.05 mmol, 15.8 mg), 1-phenyl-1H-pyrazole (1 mmol, 144.2 mg), styryl acetate (3 mmol, 486.6 mg) and toluene (1.5 mL) were added. The mixture was heated by an oil bath and reacted under reflux condition for 50 hours. 50 hours after, the reaction solution was left to cool to room temperature, then, triethylamine (0.3 mL) was added. Isolation of the product was carried out by silica gel column chromatography (i.d.=30 mm; length=170-250 mm; hexane:EtOAc:Et$_3$N=9:1:0.1; 25 mL each). A subject substance 1-(2-styrylphenyl)-1H-pyrazole was obtained with a yield of 56%.

IR (neat) 3027 m, 1598 w, 1573 w, 1515 s, 1496 s, 1461 s, 1415 w, 1394 s, 1328 m, 1191 w, 1095 w, 1045 m, 1020 w, 964 m, 937 m, 755 s, 728 m, 692 s, 622 w, 551 w, 522 m, cm$^{-1}$ $^1$H NMR (CDCl$_3$) d 6.470 (s, 1 H, ArH), 6.937 (d, J=16.5 Hz, 1 H), 7.056 (d, J=16.5 Hz, 1 H), 7.26-7.46 (m, 8H, ArH), 7.655 (d, J=2.2 Hz, 1 H, ArH), 7.75-7.78 (m, 2 H, ArH);

$^{13}$C NMR (CDCl$_3$) d 106.52, 123.77, 126.20, 126.44, 126.58, 127.83, 128.01, 128.28, 128.53, 131.09, 131.42, 132.84, 136.84, 138.60, 140.62;

MS m/z (% relative intensity) 246 (M$^+$, 35), 245 (41), 218 (12), 217 (14), 170 (11), 169 (100), 168 (13), 89 (11), 77 (10), 76 (13), 51 (14)

Elemental Analysis Anal. Calcd for $C_{17}H_{14}N_2$: C, 82.90; H, 5.73; N, 11.37%. Found: C, 82.70; H, 5.67; N, 11.27%.

Under this reaction condition, 1-(2,6-distyrylphenyl)-1H-pyrazole carrying two addition-reacted styryl groups was also obtained with a yield of 15%.

IR (KBr) 3133 m, 3079 w, 3043 m, 1625 m, 1581 m, 1511 m, 1492 m, 1461 s, 1415 m, 1390 m, 1328 m, 1213 m, 1072 m, 1054 m, 1022 m, 962 s, 941 m, 854 w, 796 s, 775 s, 736 s, 690 s, 624 w, 553 w, 526 m, 505 m, $cm^{-1}$ $^1$H NMR (CDCl$_3$) d 6.492 (d, J=16.4 Hz, 2 H), 6.538 (d, J=2.2 Hz, 1 H, ArH), 7.023 (d, J=15.9 Hz, 2 H), 7.21-7.31 (m, 10 H, ArH), 7.481 (t, J=7.6 Hz, 1 H, ArH), 7.555 (d, J=1.9 Hz, 1 H, ArH), 7.710 (d, J=7.8 Hz, 2 H, ArH), 7.866 (d, J=1.6 Hz, 1 H, ArH)

$^{13}$C NMR (CDCl$_3$) d 106.47, 123.08, 124.73, 126.69, 12796, 128.61, 129.36, 131.53, 132.93, 136.18, 136.60, 136.90, 140.67;

MS m/z (% relative intensity) 349 (22), 348 (M$^+$, 98), 347 (100), 272 (19), 271 (84), 268 (10), 254 (12), 241 (13), 193 (13), 165 (10), 152 (11), 135 (24), 134 (10), 115 (10), 77 (17), 51 (15)

Elemental Analysis Anal. Calcd for $C_{25}H_{20}N_2$: C, 86.17; H, 5.79; N, 8.04%. Found: C, 85.93; H, 5.72; N, 8.03%.

EXAMPLE 3

Production of 2-(2,6-distyrylphenyl)-pyridine

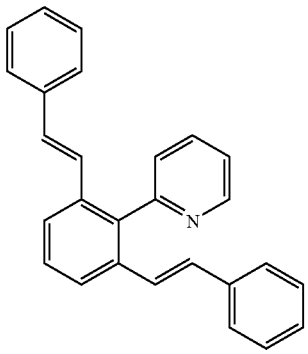

A Teflon-coated magnetic stirring rod was placed in a 10 mL two-necked flask which was then equipped with a reflux condenser. The reflux condenser was connected to a pressure reduced/nitrogen line and the whole apparatus was dried with heating under reduced pressure. Thereafter, N$_2$ gas was charged in the reaction apparatus and the whole reaction apparatus was purged with nitrogen. The reaction vessel was left to cool to room temperature, then, Ru(cod)(cot) complex (0.05 mmol, 15.8 mg), 2-phenylpyridine (1 mmol, 155.2 mg), styryl acetate (5 mmol, 811.0 mg) and toluene (1.5 mL) were added. The mixture was heated by an oil bath and reacted under reflux condition for 72 hours. 72 hours after, the reaction solution was left to cool to room temperature, then, triethylamine (0.3 mL) was added to make it basic, and the reaction mixture was purified by silica gel column chromatography (i.d.=30 mm; length=170-250 mm; hexane:EtOAc: Et$_3$N=8:1:0.1; 25 mL each). A subject substance 2-(2,6-distyrylphenyl)-pyridine was obtained with a yield of 93%.

$^1$H NMR (CDCl$_3$) d 6.752 (d, J=16.2 Hz, 2 H, Vinyl H), 6.984 (d, J=16.2 Hz, 2 H, Vinyl H), 7.15-7.36 (m, 12 H, ArH), 7.432 (t, J=7.8 Hz, 1 H, ArH), 7.696 (d, J=7.8 Hz, 2 H, ArH), 7.761 (t, J=7.8 Hz, 1 H, ArH), 8.800 (d, J=4.6 Hz, 1 H, ArH)

$^{13}$C NMR (CDCl$_3$) d 122.02, 124.71, 126.28, 126.39, 126.92, 127.40, 128.40, 129.96, 135.93, 136.39, 137.25, 138.46, 149.40, 157.96

MS m/z (% relative intensity) 360 (12), 359 (M$^+$, 37), 357 (11), 283 (21), 282 (100), 267 (11), 204 (24), 191 (12), 140 (78), 133 (15), 58 (15), 51 (12)

EXAMPLE 4

Production of 2-(2-styrylphenyl)-pyridine

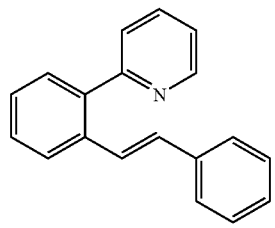

A Teflon-coated magnetic stirring rod was placed in a 10 mL two-necked flask which was then equipped with a reflux condenser. The reflux condenser was connected to a pressure reduced/nitrogen line, and the whole apparatus was dried with heating under reduced pressure. Thereafter N$_2$ gas was charged in the reaction apparatus and the whole reaction apparatus was purged with nitrogen. The reaction vessel was left to cool to room temperature, then, Ru(cod)(cot) complex (0.05 mmol, 15.8 mg), 2-phenylpyridine (1 mmol, 155.2 mg), styryl acetate (3 mmol, 486.6 mg) and toluene (1.5 mL) were added. The mixture was heated by an oil bath and reacted under reflux condition for 32 hours. 32 hours after, the reaction solution was left to cool to room temperature, then, triethylamine (0.3 mL) was added. Isolation of the product was carried out by silica gel column chromatography (i.d.=30 mm; length=170-250 mm; hexane:EtOAc:Et$_3$N=9:1:0.1; 25 mL each). A subject substance 2-(2-styrylphenyl)-pyridine was obtained with a yield of 69%.

$^1$H NMR (CDCl$_3$) 7.061 (d, J=16.2 Hz, 1 H, Vinyl H), 7.20-7.47 (m, 10 H, Vinyl H, ArH), 7.563 (d, J=7.0 Hz, 1H, ArH), 7.72-7.78 (m, 2 H, ArH), 8.753 (d, J=4.6 Hz, 1 H, ArH);

$^{13}$C NMR (CDCl$_3$) d 121.66, 124.86, 126.01, 126.36, 127.26, 127.31, 127.46, 128.37, 128.44, 129.82, 129.98, 135.42, 135.82, 137.27, 139.22, 149.21, 158.48;

MS m/z (% relative intensity) 257 (M$^+$, 10), 181 (14), 180 (100), 152 (10), 127 (23), 51 (13)

EXAMPLE 5

Production of 2-(5-methyl-2-styryl-phenyl)-pyridine

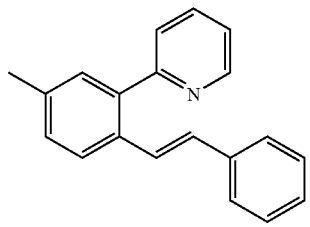

A Teflon-coated magnetic stirring rod was placed in a 10 mL two-necked flask which was then equipped with a reflux condenser. The reflux condenser was connected to a pressure reduced/nitrogen line and the whole apparatus was dried with heating under reduced pressure. Thereafter, $N_2$ gas was charged in the reaction apparatus and the whole reaction apparatus was purged with nitrogen. The reaction vessel was left to cool to room temperature, then, Ru(cod)(cot) complex (0.05 mmol, 15.8 mg), 2-m-tolylpyridine (1 mmol, 169.2 mg), styryl acetate (3 mmol, 486.6 mg) and toluene (1.5 mL) were added. The mixture was heated by an oil bath and reacted under reflux condition for 50 hours. 50 hours after, the reaction solution was left to cool to room temperature, then, triethylamine (0.3 mL) was added. Isolation of the product was carried out by silica gel column chromatography (i.d.=30 mm; length=170-250 mm; hexane:EtOAc:$Et_3N$=9:1:0.1; 25 mL each). A subject substance 2-(5-methyl-2-styrylphenyl)-pyridine was obtained with a yield of 98%.

$^1$H NMR ($CDCl_3$) d 2.415 (s, 3 H, $CH_3$), 7.017 (d, J=16.2 Hz, 1 H, Vinyl H), 7.21-7.46 (m, 10 H, ArH, Vinyl H), 7.663 (d, J=7.8 Hz, 1 H, ArH), 7.731 (t, J=7.8 Hz, 1 H, ArH), 8.749 (d, J=4.6 Hz, 1 H, ArH);

MS m/z (% relative intensity) 271 ($M^+$, 11), 195 (14), 194 (100), 127 (24)

EXAMPLE 6

Production of 2-(2-methyl-6-styrylphenyl)-pyridine

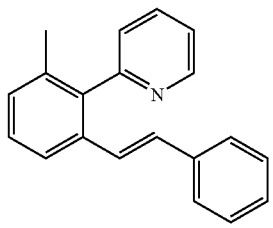

A Teflon-coated magnetic stirring rod was placed in a 4 mL pressure proof screw vial, dried with heating, then, $N_2$ gas was allowed to flow through the reaction apparatus for several minutes to purge the whole reaction apparatus with nitrogen. The reaction vessel was left to cool to room temperature, then, under a nitrogen flow, into the reaction vessel was added Ru(cod)(cot) complex (0.05 mmol, 15.08 mg), 2-o-tolylpyridine (1 mmol, 169 mg), styryl acetate (3 mmol, 486.6 mg) and dioxane (1.0 mL), and the reaction vessel was sealed. The mixture was heated at 100° C. by an oil bath and reacted for 40 hours. 40 hours after, the reaction solution was left to cool to room temperature, then, an internal standard was added, and the product was quantified by gas chromatography. Isolation of the product was carried out by silica gel column chromatography (i.d.=30 mm; length=170-250 mm; hexane:EtOAc:$Et_3N$=8:1:0.1; 25 mL each). A subject substance 2-(2-methyl-6-styrylphenyl)-pyridine was obtained with a yield of 97%.

IR (neat) 3056 s, 3027 s, 2923 m, 1585 s, 1563 s, 1494 s, 1455 s, 1423 s, 1378 w, 1326 w, 1278 m, 1224 m, 1149 m, 1091 w, 1052 m, 1025 s, 985 m, 962 s, 782 s, 742 s, 692 s, 649 w, 620 m, 553 m, 522 m, $cm^{-1}$ $^1$H NMR ($CDCl_3$) d 2.097 (s, 3 H, $CH_3$), 6.690 (d, J=16.5 Hz, 1 H, Vinyl H), 6.945 (d, J=16.5 Hz, 1 H, Vinyl H), 7.14-7.35 (m, 9 H, ArH), 7.607 (d, J=7.6 Hz, 1 H, ArH), 7.770 (t, J=7.6 Hz, 1 H, ArH), 8.761 (d, J=4.9 Hz, 1 H, ArH)

$^{13}$C NMR ($CDCl_3$) d 20.26, 121.68, 122.77, 125.24, 126.23, 127.02, 127.18, 127.96, 128.27, 129.19, 129.52, 135.73, 135.95, 136.15, 137.26, 149.31, 158.71

MS m/z (% relative intensity) 272 (10), 271 ($M^+$, 47), 270 (15), 195 (16), 194 (100), 127 (15), 51 (18)

EXAMPLE 7

Production of 4,4-dimethyl-2-(2-methyl-6-styryl-phenyl)-4,5-dihydro-oxazole

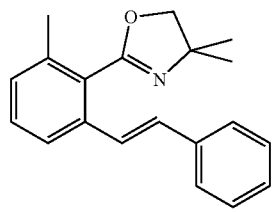

A Teflon-coated magnetic stirring rod was placed in a 10 mL two-necked flask which was then equipped with a reflux condenser. The reflux condenser was connected to a pressure reduced/nitrogen line and the whole apparatus was dried with heating under reduced pressure. Thereafter, $N_2$ gas was charged in the reaction apparatus and the whole reaction apparatus was purged with nitrogen. The reaction vessel was left to cool to room temperature, then, Ru(cod)(cot) complex (0.05 mmol, 15.8 mg), 4,4-dimethyl-2-(2-methylphenyl)-4,5-dihydroxazole (1 mmol, 189.3 mg), styryl acetate (3 mmol, 486.6 mg), 2,6-lutidine (2 mmol, 214.3 mg) and toluene (1.0 mL) were added. The mixture was heated by an oil bath and reacted under reflux condition for 40 hours. 40 hours after, the reaction solution was left to cool to room temperature, then, triethylamine (0.3 mL) was added. Isolation of the product was carried out by silica gel column chromatography (i.d.=30 mm; length=170-250 mm; hexane:EtOAc:$Et_3N$=9:1:0.1; 25 mL each).

A subject substance 4,4-dimethyl-2-(2-methyl-6-styryl-phenyl)-4,5-dihydro-oxazole was obtained with a yield of 69%.

IR (KBr) 3064 m, 2967 s, 2925 m, 2869 m, 1656 s, 1592 m, 1494 m, 1461 s, 1359 m, 1292 s, 1211 m, 1187 m, 1103 m, 1043 s, 958 s, 919 m, 869 w, 821 w, 781 m, 742 s, 709 s, 692 m, 619 w, 557 w, 512 w, 491 w, $cm^{-1}$ $^1$H NMR ($CDCl_3$) d 1.469 (s, 6 H, $CH_3$), 2.368 (s, 3 H, $CH_3$), 4.410 (s, 2 H, $CH_2$), 7.037 (d, J=16.2 Hz, 1 H, Vinyl H), 7.115 (d, J=7.6 Hz, 1 H, ArH), 7.24-7.37 (m, 5 H, ArH, Vinyl H), 7.44-7.47 (m, 2 H, ArH), 7.530 (d, J=7.8 Hz, 1 H, ArH)

$^{13}$C NMR ($CDCl_3$) d 19.66, 28.64, 68.18, 79.01, 122.59, 125.95, 126.43, 127.55, 128.55, 128.94, 129.42, 130.50, 136.56, 137.17, 137.31, 161.57

MS m/z (% relative intensity) 291 ($M^+$, 6), 215 (16), 214 (100), 142 (12), 55 (24)

EXAMPLE 8

Production of 2-(2-styrylthiophen-3-yl)-pyridine

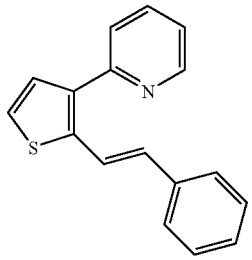

A Teflon-coated magnetic stirring rod was placed in a 10 mL two-necked flask which was then equipped with a reflux condenser. The reflux condenser was connected to a pressure reduced/nitrogen line and the whole apparatus was dried with heating under reduced pressure. Thereafter N$_2$ gas was charged in the reaction apparatus and the whole reaction apparatus was purged with nitrogen. The reaction vessel was left to cool to room temperature, then, Ru(cod)(cot) complex (0.05 mmol, 15.8 mg), 2-(thiophen-3-yl)-pyridine (1 mmol, 161.2 mg), styryl acetate (3 mmol, 486.6 mg) and toluene (1.5 mL) were added. The mixture was heated by an oil bath and reacted under reflux condition for 50 hours. 50 hours after, the reaction solution was left to cool to room temperature, then, triethylamine (0.3 mL) was added. Isolation of the product was carried out by silica gel column chromatography (i.d.=30 mm; length=170-250 mm; hexane:EtOAc:Et$_3$N=9:1:0.1; 25 mL each).

A subject substance 2-(2-styryl-thiophen-3-yl)-pyridine was obtained with a yield of 89%.

$^1$H NMR (CDCl$_3$) d 7.066 (d, J=16.5 Hz, 1 H, Vinyl H), 7.19-7.60 (m, 10 H, ArH, Vinyl H), 7.736 (td, J=7.6 Hz, J=1.9. Hz, 1 H, ArH), 8.693 (d, J=4.9 Hz, 1 H, ArH)

MS m/z (% relative intensity) 263 (M$^+$, 8), 187 (12), 186 (100), 51 (13)

EXAMPLE 9

Production of 4-(2,6-distyrylphenyl)-2-methylthiazole

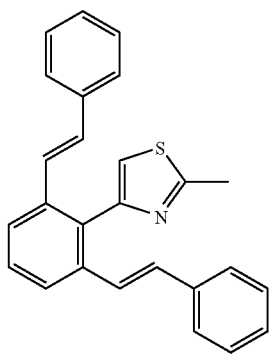

A Teflon-coated magnetic stirring rod was placed in a 10 mL two-necked flask which was then equipped with a reflux condenser. The reflux condenser was connected to a pressure reduced/nitrogen line and the whole apparatus was dried with heating under reduced pressure. Thereafter, N$_2$ gas was charged in the reaction apparatus and the whole reaction apparatus was purged with nitrogen. The reaction vessel was left to cool to room temperature, then, Ru(cod)(cot) complex (0.05 mmol, 15.8 mg), 2-methyl-4-phenylthiazole (1 mmol, 175.2 mg), styryl acetate (3 mmol, 486.6 mg) and toluene (1.5 mL) were added. The mixture was heated by an oil bath and reacted under reflux condition for 50 hours. The reaction solution was left to cool to room temperature, then, triethylamine (0.3 mL) was added. Isolation of the product was carried out by silica gel column chromatography (i.d.=30 mm; length=250 mm; hexane:EtOAc:Et$_3$N=10:1:0.1; mL each).

A subject product 4-(2,6-distyrylphenyl)-2-methylthiazole was obtained with a yield of 60%.

$^1$H NMR (CDCl$_3$) d 2.835 (s, 3 H, CH$_3$), 6.906 (d, J=16.2 Hz, 2 H, Vinyl H), 7.005 (d, J=16.4 Hz, 2 H, Vinyl H), 7.051 (s, 1 H, ArH), 7.18-7.36 (m, 10 H, ArH), 7.417 (t, J=7.8 Hz, 1 H, ArH), 7.680 (d, J=7.8 Hz, 2 H, ArH);

$^{13}$C NMR (CDCl$_3$) d 19.33, 118.35, 124.50, 126.33, 127.19, 127.28, 128.34, 129.70, 133.01, 137.29, 137.50, 151.72, 164.93;

IR (KBr) 3052 m, 3025 m, 1594 m, 1569 m, 1490 s, 1444 s, 1326 w, 1282 m, 1191 m, 1162 s, 1072 w, 1051 w, 958 s, 844 w, 788 s, 736 s, 690 s, 649 m, 551 w, 532 m, 501 m, cm$^{-1}$

MS m/z (% relative intensity) 380 (10), 379 (M$^+$, 32), 302 (26), 289 (27), 288 (100), 243 (10), 242 (10), 150 (29), 59 (24)

Elemental Analysis: Anal. Calcd for C$_{26}$H$_{21}$NS: C, 82.28; H, 5.58; N, 3.69; S, 8.45%. Found: C, 82.17; H, 5.57; N, 3.58; S, 8.45%.

Under this reaction condition, 2-methyl-4-(2-styrylphenyl)thiazole carrying one added styryl group was also obtained with a yield of 22%.

$^1$H NMR (CDCl$_3$) d 2.806 (s, 3 H, CH$_3$), 7.038 (d, J=16.2 Hz, 1 H, Vinyl H), 7.112 (s, 1 H, ArH), 7.22-7.47 (m, 8H, ArH), 7.696 (t, J=7.0 Hz, 2 H, ArH)

$^{13}$C NMR (CDCl$_3$) d 19.29, 116.85, 126.45, 126.56, 127.52, 127.62, 128.08, 128.22, 128.64, 129.94, 130.00, 133.84, 135.98, 137.56, 154.00, 165.22

IR (neat) 3052 s, 3023 s, 2919 m, 1598 m, 1494 s, 1448 s, 1434 s, 1307 m, 1214 w, 1170 s, 1101 w, 1027 s, 962 s, 856 w, 790 w, 759 s, 728 m, 692 s, 647 w, 547 m, 512 m, cm$^{-1}$ MS m/z (% relative intensity) 277 (M$^+$, 27), 236 (13), 235 (11), 203 (10), 202 (24), 201 (17), 200 (100), 186 (48), 115 (14), 101 (11), 59 (11), 51 (10)

HRMS Calcd for C$_{18}$H$_{15}$NS: 277.0925. Found: 277.0931.

EXAMPLE 10

Production of (E)-10-styrylbenzo[h]quinoline

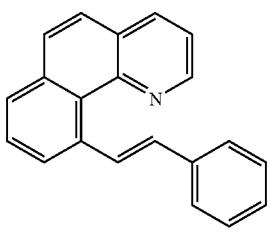

A Teflon-coated magnetic stirring rod was placed in a 10 mL two-necked flask which was then equipped with a reflux condenser. The reflux condenser was connected to a pressure reduced/nitrogen line and the whole apparatus was dried with heating under reduced pressure. Thereafter, N$_2$ gas was charged in the reaction apparatus and the whole reaction apparatus was purged with nitrogen. The reaction vessel was left to cool to room temperature, then, Ru(cod)(cot) complex (0.05 mmol, 15.8 mg), benzo[h]quinoline (1 mmol, 179.2 mg), styryl acetate (3 mmol, 486.6 mg) and toluene (1.5 mL) were added. The mixture was heated by an oil bath and reacted under reflux condition for 50 hours. The reaction solution was left to cool to room temperature, then, triethylamine (0.3 mL) was added. Isolation of the product was carried out by silica gel column chromatography (i.d.=30 mm; length=220 mm; hexane:EtOAc:Et$_3$N=8:1:0.1; mL each).

A subject product (E)-10-styrylbenzo[h]quinoline was obtained with a yield of 37%.

$^1$H NMR (CDCl$_3$) d 6.954 (d, J=16.2 Hz, 1 H, Vinyl H), 7.295 (d, J=7.2 Hz, 1 H, ArH), 7.420 (t, J=7.5 Hz, 2 H, ArH), 7.498 (dd, J=7.8 Hz, 4.3 Hz, 1 H, ArH), 7.66-7.72 (m, 4 H, ArH), 7.835 (d, J=7.8 Hz, 1 H, ArH), 7.899 (t, J=6.4 Hz, 2 H, ArH), 8.186 (dd, J=5.1 Hz, 1.6 Hz, 1 H, ArH), 9.056 (d, J=1.6 Hz, 1 H, ArH), 9.102 (d, J=15.9 Hz, 1 H, Vinyl H)

$^{13}$C NMR (CDCl$_3$) d 120.87, 125.71, 126.73, 126.97, 127.58, 127.65, 127.69, 128.12, 128.15, 128.60, 128.76, 134.66, 134.92, 135.63, 138.55, 138.77, 147.83, 148.05

IR (neat) 3048 m, 3023 m, 1619 m, 1598 m, 1587 m, 1565 m, 1492 s, 1448 m, 1417 s, 1394 m, 1324 m, 1124 w, 950 s, 908 w, 869 m, 854 m, 833 s, 819 m, 761 s, 748 s, 727 s, 692 s, 640 m, 557 w, 487 w, cm$^{-1}$ MS m/z (% relative intensity) 281 (M$^+$, 8), 205 (15), 204 (100), 139 (10), 51 (10)

Under this reaction condition, (Z)-10-styrylbenzo[h] quinoline as a steric chemical isomer was also obtained with a yield of 15%.

$^1$H NMR (CDCl$_3$) d 6.686 (d, J=12.1 Hz, 1 H, Vinyl H), 6.95-7.15 (m, 5 H, ArH), 7.43-7.56 (m, 3 H, ArH), 7.702 (d, J=8.3 Hz, 1 H, ArH), 7.82-7.86 (m, 2 H, ArH), 7.904 (d, J=11.9 Hz, 1 H, Vinyl H), 8.182 (dd, J=7.8 Hz, 1.3 Hz, 1 H, ArH), 9.035 (d, J=2.7 Hz, 1 H, ArH)

$^{13}$C NMR (CDCl$_3$) d 121.00, 124.56, 125.51, 126.00, 126.73, 127.39, 127.51, 127.73, 127.80, 128.54, 129.30, 129.58, 130.88, 134.92, 135.36, 136.30, 137.24, 137.79, 147.84

IR (neat) 3048 m, 3021 m, 1619 m, 1598 m, 1587 m, 1565 m, 1509 m, 1492 s, 1440 m, 1421 s, 1394 m, 1324 m, 1120 w, 1074 w, 979 w, 910 m, 867 m, 848 m, 833 s, 773 s, 742 s, 730 s, 694 s, 657 m, 470 w, cm$^{-1}$ MS m/z (% relative intensity) 281 (M$^+$, 16), 205 (15), 204 (100), 51 (10)

EXAMPLE 11

Production of 2-(2,5-distyryl-1H-pyrrol-1-yl)pyridine

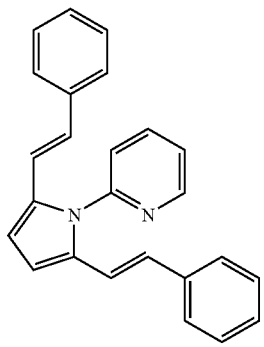

A Teflon-coated magnetic stirring rod was placed in a 10 mL two-necked flask which was then equipped with a reflux condenser. The reflux condenser was connected to a pressure reduced/nitrogen line and the whole apparatus was dried with heating under reduced pressure. Thereafter, N$_2$ gas was charged in the reaction apparatus and the whole reaction apparatus was purged with nitrogen. The reaction vessel was left to cool to room temperature, then, Ru(cod)(cot) complex (0.05 mmol, 15.8 mg), 2-(1H-pyrrol-1-yl)pyridine (1 mmol, 144.2 mg), styryl acetate (5 mmol, 811.0 mg) and toluene (1.5 mL) were added. The mixture was heated by an oil bath and reacted under reflux condition for 50 hours. The reaction solution was left to cool to room temperature, then, triethylamine (0.3 mL) was added. Isolation of the product was carried out by silica gel column chromatography (i.d.=30 mm; length=300 mm; hexane:EtOAc:Et$_3$N=10:1:0.1; mL each).

A subject product 2-(2,5-distyryl-1H-pyrrol-1-yl)pyridine was obtained with a yield of 92%.

$^1$H NMR (CDCl$_3$) d 6.709 (d, J=16.4 Hz, 2 H, Vinyl H), 6.710 (s, 2 H, ArH), 6.843 (d, J=16.5 Hz, 2 H, Vinyl H), 7.12-7.35 (m, 11 H, ArH), 7.42-7.47 (m, 1 H, ArH), 7.908 (td, J=8.1 Hz, 1.9 Hz, 1 H, ArH), 8.755 (d, J=4.8 Hz, 1 H, ArH)

$^{13}$C NMR (CDCl$_3$) d 108.69, 117.66, 123.23, 123.51, 125.98, 126.61, 126.98, 128.52, 134.20, 137.65, 138.29, 149.65, 150.93

IR (KBr) 3021 w, 1621 m, 1585 m, 1571 m, 1492 w, 1469 s, 1436 s, 1407 m, 1342 w, 1328 w, 1249 w, 1022 w, 950 m, 796 m, 767 m, 746 m, 692 s, 555 m, 507 w, cm$^{-1}$

MS m/z (% relative intensity) 349 (27), 348 (M$^+$, 100), 347 (31), 272 (10), 271 (37), 256 (12), 173 (20), 173 (15), 134 (26), 115 (10), 78 (27), 51 (14)

Elemental Analysis: Anal. Calcd for C$_{25}$H$_{20}$N$_2$: C, 86.17; H, 5.79; N, 8.04%. Found: C, 85.89; H, 5.75; N, 7.96%.

EXAMPLE 12

Production of 2-(2,6-distyrylphenyl)pyrimidine

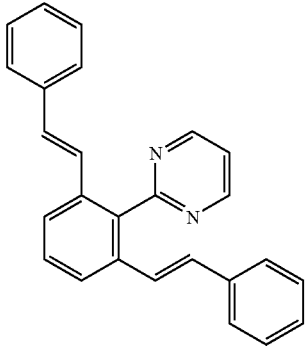

A Teflon-coated magnetic stirring rod was placed in a 10 mL two-necked flask which was then equipped with a reflux condenser. The reflux condenser was connected to a pressure reduced/nitrogen line and the whole apparatus was dried with heating under reduced pressure. Thereafter, $N_2$ gas was charged in the reaction apparatus and the whole reaction apparatus was purged with nitrogen. The reaction vessel was left to cool to room temperature, then, Ru(cod)(cot) complex (0.05 mmol, 15.8 mg), 2-phenylpyrimidine (1 mmol, 156.2 mg), styryl acetate (5 mmol, 811.0 mg) and toluene (1.5 mL) were added. The mixture was heated by an oil bath and reacted under reflux condition for 36 hours. The reaction solution was left to cool to room temperature, then, triethylamine (0.3 mL) was added. Isolation of the product was carried out by silica gel column chromatography (i.d.=30 mm; length 270 mm; hexane:EtOAc:$Et_3N$=10:1:0.1; 50 mL each).

A subject product 2-(2,6-distyrylphenyl)pyrimidine was obtained with a yield of 90%.

$^1$H NMR (CDCl$_3$) d 6.736 (d, J=15.9 Hz, 2 H, Vinyl H), 6.982 (d, J=15.9 Hz, 2 H, Vinyl H), 7.16-7.28 (m, 10 H, ArH), 7.352 (t, J=4.8 Hz, 1 H, ArH), 7.463 (t, J=7.8 Hz, 1 H, ArH), 7.694 (d, J=8.1 Hz, 2 H, ArH), 8.938 (d, J=4.8 Hz, 2 H, ArH)

$^{13}$C NMR (CDCl$_3$) 119.18, 125.14, 126.59, 127.60, 128.52, 129.06, 130.80, 136.38, 137.38, 157.17, 167.51

IR (KBr) 3021 m, 1596 w, 1556 s, 1492 m, 1444 m, 1403 s, 1322 w, 1155 w, 1072 w, 1031 w, 981 w, 960 s, 833 w, 792 m, 736 s, 690 s, 659 w, 632 w, 532 w, 505 w, cm$^{-1}$

MS m/z (% relative intensity) 361 (13), 360 (M$^+$, 47), 359 (19), 284 (23), 283 (100), 206 (10), 140 (50), 133 (175)

Elemental Analysis: Anal. Calcd for $C_{26}H_{20}N_2$: C, 86.64; H, 5.59; N, 7.77%. Found: C, 86.42; H, 5.70; N, 7.70%.

EXAMPLE 13

Production of (E)-2-(2-styryl-6-(trifluoromethyl)phenyl)pyridine

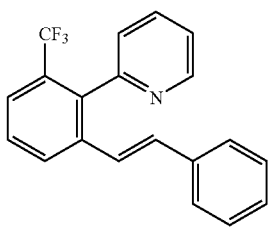

A Teflon-coated magnetic stirring rod was placed in a 10 mL two-necked flask which was then equipped with a reflux condenser. The reflux condenser was connected to a pressure reduced/nitrogen line and the whole apparatus was dried with heating under reduced pressure. Thereafter, $N_2$ gas was charged in the reaction apparatus and the whole reaction apparatus was purged with nitrogen. The reaction vessel was left to cool to room temperature, then, Ru(cod)(cot) complex (0.05 mmol, 15.8 mg), 2-(2-(trifluoromethyl)phenyl)pyridine (1 mmol, 223.2 mg), styryl acetate (3 mmol, 486.6 mg) and toluene (1.5 mL) were added. The mixture was heated by an oil bath and reacted under reflux condition for 30 hours. The reaction solution was left to cool to room temperature, then, triethylamine (0.3 mL) was added. Isolation of the product was carried out by silica gel column chromatography (i.d.=30 mm; length=300 mm; hexane:EtOAc:$Et_3N$=10:1:0.1; mL each).

A subject product (E)-2-(2-styryl-6-(trifluoromethyl)phenyl)pyridine was obtained with a yield of 93%.

$^1$H NMR (CDCl$_3$) d 6.572 (d, J=16.2 Hz, 1 H, Vinyl H), 6.987 (d, J=16.2 Hz, 1 H, Vinyl H), 7.15-7.40 (m, 7 H, ArH), 7.532 (t, J=8.1 Hz, 1 H, ArH), 7.684 (d, J=7.8 Hz, 1 H, ArH), 7.784 (td, J=7.6 Hz, 4.3 Hz, 1 H, ArH) 7.938 (d, J=8.1 Hz, 1 H, ArH), 8.747 (d, J=4.6 Hz, 1 H, ArH)

IR (neat) 3079 s, 3006 s, 1953 w, 1812 w, 1635 m, 1567 s, 1492 m, 1479 m, 1450 s, 1425 s, 1332 s, 1280 m, 1245 m, 1211 m, 1054 m, 1024 m, 985 m, 960 m, 900 m 852 w, 804 m, 692 m, 669 m, 619 w, 503 w, cm$^{-1}$ Elemental Analysis Anal. Calcd for $C_{20}H_{14}F_3N$: C, 73.84; H, 4.34; F, 17.52; N, 4.31%. Found: C, 73.64; H, 4.22; F, 17.66; N, 4.36%.

EXAMPLE 14

Production of (E)-2-(2-methoxy-6-styrylphenyl)pyridine

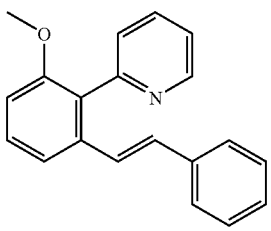

A Teflon-coated magnetic stirring rod was placed in a 10 mL two-necked flask which was then equipped with a reflux condenser. The reflux condenser was connected to a pressure reduced/nitrogen line and the whole apparatus was dried with heating under reduced pressure. Thereafter, $N_2$ gas was charged in the reaction apparatus and the whole reaction apparatus was purged with nitrogen. The reaction vessel was left to cool to room temperature, then, Ru(cod)(cot) complex (0.05 mmol, 15.8 mg), 2-(2-methoxyphenyl)pyridine (1 mmol, 185.2 mg), styryl acetate (3 mmol, 486.6 mg) and toluene (1.5 mL) were added. The mixture was heated by an oil bath and reacted under reflux condition for 20 hours. The reaction solution was left to cool to room temperature, then, triethylamine (0.3 mL) was added. Isolation of the product was carried out by silica gel column chromatography (i.d.=30 mm; length=220 mm; hexane:EtOAc:$Et_3N$=3:1:0.1; mL each).

A subject product (E)-2-(2-methoxy-6-styrylphenyl)pyridine was obtained with a yield of 88%.

$^1$H NMR (CDCl$_3$) d 3.747 (s, 3 H, CH$_3$), 6.747 (d, J=15.9 Hz, 1 H, Vinyl H), 6.915 (dd, J=7.0 Hz, 2.1 Hz, 1 H, ArH), 6.985 (d, J=15.9 Hz, 1 H, Vinyl H), 7.16-7.42 (m, 9H, ArH), 7.749 (t, J=7.6 Hz, 1 H, ArH), 8.759 (d, J=4.6 Hz, 1 H, ArH)

$^{13}$C NMR (CDCl$_3$) d 55.90, 109.91, 117.82, 121.79, 126.27, 126.44, 126.68, 127.38, 128.39, 129.02, 129.08, 130.05, 135.72, 137.31, 137.44, 149.24, 156.09, 157.02

IR (neat) 3077 s, 3002 s, 2935 s, 2834 s, 1631 m, 1594 s, 1563 s, 1490 s, 1427 s, 1247 s, 1182 m, 1149 m, 1024 m, 962 s, 931 m, 850 w, 782 s, 750 s, 732 s, 694 s, 605 m, 561 m, 539 w, 501 m, cm$^{-1}$ MS m/z (% relative intensity) 287 (M$^+$, 23), 211 (15), 210 (100), 195 (36), 167 (20), 127 (23), 120 (14), 51 (12)

Elemental Analysis: Anal. Calcd for C$_{20}$H$_{17}$NO: C, 83.59; H, 5.96; N, 4.87; O, 5.57%. Found: C, 83.35; H, 5.94; N, 4.84%.

EXAMPLE 15

Production of (E)-4-(3-methylpyridin-2-yl)-3-styryl-benzonitrile

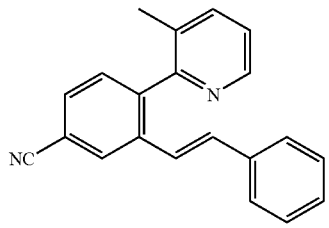

A Teflon-coated magnetic stirring rod was placed in a 10 mL two-necked flask which was then equipped with a reflux condenser. The reflux condenser was connected to a pressure reduced/nitrogen line and the whole apparatus was dried with heating under reduced pressure. Thereafter, N$_2$ gas was charged in the reaction apparatus and the whole reaction apparatus was purged with nitrogen. The reaction vessel was left to cool to room temperature, then, Ru(cod)(cot) complex (0.05 mmol, 15.8 mg), 4-(3-methylpyridine-2-yl)benzonitrile (1 mmol, 194.2 mg), styryl acetate (3 mmol, 486.6 mg) and toluene (1.5 mL) were added. The mixture was heated by an oil bath and reacted under reflux condition for 30 hours. The reaction solution was left to cool to room temperature, then, triethylamine (0.3 mL) was added. Isolation of the product was carried out by silica gel column chromatography (i.d.=30 mm; length=250 mm; hexane:EtOAc:Et$_3$N=9:1:0.1; mL each).

A subject product (E)-4-(3-methylpyridin-2-yl)-3-styryl-benzonitrile was obtained with a yield of 86%.

$^1$H NMR (CDCl$_3$) d 2.097 (s, 3 H, CH$_3$), 6.681 (d, J=16.2 Hz, 1 H, Vinyl H), 7.060 (d, J=16.2 Hz, 1 H, Vinyl H), 7.23-7.33 (m, 6 H, ArH), 7.390 (d, J=8.1 Hz, 1 H, ArH), 7.61-7.65 (m, 2 H, ArH), 8.055 (s, 1 H, ArH), 8.583 (d, J=4.6 Hz, 1 H, ArH)

$^{13}$C NMR (CDCl$_3$) d 19.09, 112.38, 118.67, 123.13, 123.91, 126.69, 128.26, 128.60, 129.18, 130.28, 130.38, 131.90, 132.38, 136.32, 136.88, 138.18, 143.38, 146.99, 156.60

MS m/z (% relative intensity) 296 (M$^+$, 29), 295 (12), 220 (18), 219 (100), 65 (10), 51 (15)

Elemental Analysis: Anal. Calcd for C$_{21}$H$_{16}$N$_2$: C, 85.11; H, 5.44; N, 9.45%. Found: C, 84.91; H, 5.51; N, 9.45%.

EXAMPLE 16

Production of (E)-3-methyl-2-(2-styrylphenyl)pyridine

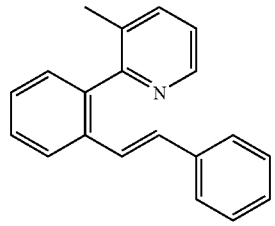

A Teflon-coated magnetic stirring rod was placed in a 10 mL two-necked flask which was then equipped with a reflux condenser. The reflux condenser was connected to a pressure reduced/nitrogen line and the whole apparatus was dried with heating under reduced pressure. Thereafter, N$_2$ gas was charged in the reaction apparatus and the whole reaction apparatus was purged with nitrogen. The reaction vessel was left to cool to room temperature, then, Ru(cod)(cot) complex (0.05 mmol, 15.8 mg), 3-methyl-2-phenylpyridine (1 mmol, 169.2 mg), styryl acetate (3 mmol, 486.6 mg) and toluene (1.5 mL) were added. The mixture was heated by an oil bath and reacted under reflux condition for 14 hours. The reaction solution was left to cool to room temperature, then, triethylamine (0.3 mL) was added. Isolation of the product was carried out by silica gel column chromatography (i.d.=30 mm; length=250 mm; hexane:EtOAc:Et$_3$N=5:1:0.1; mL each).

A subject product (E)-3-methyl-2-(2-styrylphenyl)pyridine was obtained with a yield of 93%.

$^1$H NMR (CDCl$_3$) d 2.10 (s, 3 H, CH$_3$), 6.76 (d, J=16.2 Hz, 1 H, Vinyl H), 7.01 (d, J=16.2 Hz, 1 H, Vinyl H), 7.18-7.44 (m, 9 H, ArH), 7.58 (d, J=7.2 Hz, 1 H, ArH), 7.77 (d, J=7.6 Hz, 1 H, ArH), 8.56 (d, J=4.3 Hz, 1 H, ArH)

$^{13}$C NMR (CDCl$_3$) d 19.31, 122.33, 125.17, 126.25, 126.39, 127.41, 128.14, 128.41, 129.23, 129.77, 132.05, 135.26, 137.29, 137.64, 139.53, 146.71, 158.60

IR (neat) 3056 s, 3027 s, 2923 m, 1567 s, 1494 s, 1446 s, 1421 s, 1382 m, 1328 m, 1259 m, 1216 m, 1184 m, 1159 w, 1120 m, 1099 m, 1068 m, 1024 m, 964 s, 794 s, 759 s, 736 s, 692 s, 624 m, 574 w, 539 m, 520 m, cm$^{-1}$ MS m/z (% relative intensity) 271 (M$^+$, 32), 270 (12), 195 (14), 194 (100), 134 (12), 127 (26)

Elemental Analysis: Anal. Calcd for C$_{20}$H$_{17}$N: C, 88.52; H, 6.31; N, 5.16%. Found: C, 88.25; H, 6.29; N, 5.13%.

EXAMPLE 17

Production of (E)-2-methyl-6-(2-methyl-6-styrylphenyl)pyridine

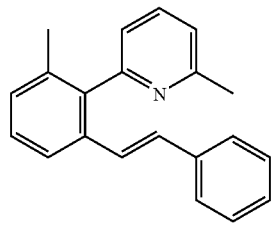

A Teflon-coated magnetic stirring rod was placed in a 10 mL two-necked flask which was then equipped with a reflux condenser. The reflux condenser was connected to a pressure reduced/nitrogen line and the whole apparatus was dried with heating under reduced pressure. Thereafter, $N_2$ gas was charged in the reaction apparatus and the whole reaction apparatus was purged with nitrogen. The reaction vessel was left to cool to room temperature, then, Ru(cod)(cot) complex (0.05 mmol, 15.8 mg), 3-methyl-2-phenylpyridine (1 mmol, 183.3 mg), styryl acetate (3 mmol, 486.6 mg) and toluene (1.5 mL) were added. The mixture was heated by an oil bath and reacted under reflux condition for 60 hours. The reaction solution was left to cool to room temperature, then, triethylamine (0.3 mL) was added. Isolation of the product was carried out by silica gel column chromatography (i.d.=30 mm; length=250 mm; hexane:EtOAc:$Et_3N$=9:1:0.1; mL each).

A subject product (E)-3-methylpyridine-2-(2-styrylphenyl)pyridine was obtained with a yield of 19%.

$^1$H NMR ($CDCl_3$) d 2.096 (s, 3 H, $CH_3$), 2.669 (s, 3 H, $CH_3$), 6.727 (d, J=16.4 Hz, 1 H, Vinyl H), 6.943 (d, J=16.2 Hz, 1 H, Vinyl H), 7.058 (d, J=7.8 Hz, 1 H, ArH), 7.11-7.33 (m, 8 H, ArH), 7.597 (d, J=7.6 Hz, 1 H, ArH), 7.651 (t, J=7.6 Hz, 1 H, ArH)

$^{13}$C NMR ($CDCl_3$) d 20.35, 24.70, 121.36, 122.35, 122.96, 126.45, 127.34, 127.49, 128.04, 128.50, 129.49, 135.91, 136.38, 136.45, 137.63, 139.82, 158.23, 158.29

IR (neat) 3058 m, 3027 m, 2923 w, 1577 s, 1494 m, 1452 s, 1375 w, 1324 w, 1222 w, 1159 w, 995 m, 962 m, 800 m, 782 s, 742 s, 694 m, 644 w, 549 w, 503 w, 468 m, $cm^{-1}$ MS m/z (% relative intensity) 285 ($M^+$, 26), 284 (12), 208 (15), 195 (14), 194 (100), 141 (16), 134 (26), 127 (10)

Industrial Applicability

According to the present invention, a compound having a nitrogen-containing heterocyclic ring and an alkenyl group at adjacent positions of an aromatic ring can be produced using an olefin compound containing no halogen as an alkenylating agent.

The invention claimed is:

1. A method of producing an aromatic compound of the following formula (3) comprising reacting a compound of the following formula (1) with an olefin compound of the following formula (2) in the presence of a ruthenium complex:

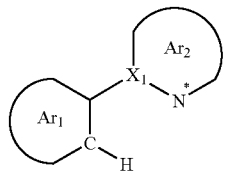

(1)

wherein, an $Ar_1$ ring represents an aromatic hydrocarbon ring or aromatic heterocyclic ring, an $Ar_2$ ring represents a heterocyclic ring containing $X_1$ and $N^*$, and the $X_1$ represents a nitrogen atom or carbon atom and the $N^*$ represents a nitrogen atom connecting via a double bond to either one of two adjacent atoms in the $Ar_2$ ring; the $Ar_1$ ring and/or the $Ar_2$ ring may optionally have a group selected from an alkyl group having 1 to 10 carbon atoms, an alkoxy group having 1 to 10 carbon atoms, an aryl group having 6 to 18 carbon atoms and an aryloxy group having 6 to 10 carbon atoms; the $Ar_1$ ring and the $Ar_2$ ring can be further connected directly or via a divalent group; and the $Ar_1$ ring is a benzene ring, naphthalene ring, anthracene ring, phenanthrene ring, pyrene ring, fluorene ring, furan ring, oxazole ring, isooxazole ring, thiophene ring, thiazole ring, isothiazole ring, pyrrole ring, imidazole ring, pyrazole ring, tetrazole ring, pyridine ring, pyrazine ring, pyrimidine ring, pyridazine ring, triazine ring, indole ring, indazole ring, quinoline ring, isoquinoline ring, purine ring, naphthyridine ring, phthalazine ring, quinoxaline ring, quinazoline ring, carbazole ring, phenanthridine ring, phenanthroline ring, acridine ring, or phenazine ring, and the $Ar_2$ ring is an imidazole ring, pyrazole ring, tetrazole ring, oxazole ring, isooxazole ring, thiazole ring, isothiazole ring, pyridine ring, pyrazine ring, pyrimidine ring, pyridazine ring, triazine ring, indole ring, indazole ring, quinoline ring, isoquinoline ring, purine ring, naphthyridine ring, phthalazine ring, quinoxaline ring, quinazoline ring, carbazole ring, phenanthridine ring, phenanthroline ring, acridine ring, or phenazine ring; or the $Ar_1$ ring and the $Ar_2$, ring form benzo[h][1,6]naphthyridine, thieno[2,3-h]quinoline, furo[2,3-h]quinoline, 7H-pyrrolo[2,3-h]quinoline, 3H-9-aza-cyclopenta[a]naphthalene, or 7H-pyrrolo[3,4-h]quinoline;

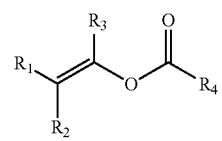

(2)

wherein, $R_1$, $R_2$, $R_3$ and $R_4$ represent each independently a hydrogen atom, an alkyl group having 1 to 10 carbon atoms or an aryl group having 6 to 18 carbon atoms; and

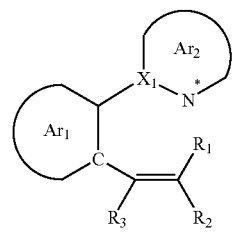

(3)

wherein, $Ar_1$, $Ar_2$, $X_1$, $N^*$, $R_1$, $R_2$ and $R_3$ represent the same meanings as described above.

2. The production method according to claim 1, wherein said compound of the formula (1) is a compound of the following formula (1'):

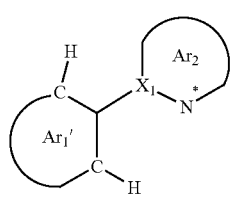

(1')

wherein, an $Ar_1'$ ring represents an aromatic hydrocarbon ring or aromatic heterocyclic ring, an $Ar_2$ ring, $X_1$ and $N^*$ represent the same meanings as described above, and the $Ar_1'$ ring and/or the Ar₂ ring optionally have a group selected from an alkyl group having 1 to 10 carbon atoms, an alkoxy group having 1 to 10 carbon atoms, an aryl group having 6 to 18 carbon atoms and an aryloxy group having 6 to 10 carbon atoms, the Ar₁' ring and the Ar₂ ring can be further connected directly or via a divalent group; and the Ar₁ ring is a benzene ring, naphthalene ring, anthracene ring, phenanthrene ring, pyrene ring, fluorene ring, furan ring, oxazole ring, isooxazole ring, thiophene ring, thiazole ring, isothiazole ring, pyrrole ring, imidazole ring, pyrazole ring, tetrazole ring, pyridine ring, pyrazine ring, pyrimidine ring, pyridazine ring, triazine ring, indole ring, indazole ring, quinoline ring, isoquinoline ring, purine ring, naphthyridine ring, phthalazine ring, quinoxaline ring, quinazoline ring, carbazole ring, phenanthridine ring, phenanthroline ring, acridine ring, or phenazine ring, and the Ar₂ ring is an imidazole ring, pyrazole ring, tetrazole ring, oxazole ring, isooxazole ring, thiazole ring, isothiazole ring, pyridine ring, pyrazine ring, pyrimidine ring, pyridazine ring, triazine ring, indole ring, indazole ring, quinoline ring, isoquinoline ring, purine ring, naphthyridine ring, phthalazine ring, quinoxaline ring, quinazoline ring, carbazole ring, phenanthridine ring, phenanthroline ring, acridine ring, or phenazine ring.

3. A method of producing an aromatic compound of the following formula (4) comprising reacting a compound of the formula (1') with an olefin compound of the formula (2) in the presence of a ruthenium complex:

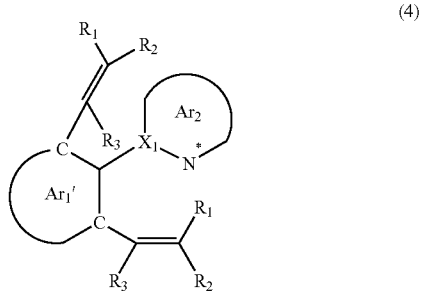

(4)

wherein, Ar₁', Ar₂, X₁, N*, R₁, R₂ and R₃ represent the same meanings as described above.

4. The production method according to claim 1, wherein the ruthenium complex is (1,5-cyclooctadiene)(1,3,5-cyclooctatriene)ruthenium.

5. An aromatic compound wherein the Ar₁ ring in the formula (3) is an aromatic heterocyclic ring containing 1 to 3 heteroatoms in the ring structure.

6. An aromatic compound wherein the Ar₁' ring in the formula (4) is an aromatic heterocyclic ring containing 1 to 3 heteroatoms in the ring structure.

7. An aromatic compound wherein the Ar₁ ring in the formula (3) is a thiophene ring.

8. An aromatic compound wherein the Ar₁' ring in the formula (4) is a thiophene ring.

9. The production method according to claim 1, wherein the ruthenium complex is ruthenium carbonyl, (cyclooctadienyl)(cyclooctatrienyl)ruthenium, or tricarbonylbis(triphenylphosphine)ruthenium.

10. The production method according to claim 1, wherein the Ar₁ ring is a benzene ring, thiophene ring or pyrrole ring, and the Ar₂ ring is a pyridine ring, pyrazole ring, oxazole ring, thiazole ring or pyrimidine ring; or the Ar₁ ring and the Ar₂ ring form benzo[h]quinoline, the Ar₁ ring and/or the Ar₂ ring optionally having a group selected from an alkyl group having 1 to 10 carbon atoms, and an alkoxy group having 1 to 10 carbon atoms.

11. The production method according to claim 2, wherein the Ar₁ ring is a benzene ring, thiophene ring or pyrrole ring, the Ar₂ ring is a pyridine ring, pyrazole ring, oxazole ring, thiazole ring or pyrimidine ring, and the Ar₁ ring and/or the Ar₂ ring optionally have a group selected from an alkyl group having 1 to 10 carbon atoms, and an alkoxy group having 1 to 10 carbon atoms.

12. The aromatic compound according to claim 5, wherein the Ar₁ ring is a thiophene ring or pyrrole ring, the Ar₂ ring is a pyridine ring, pyrazole ring, oxazole ring, thiazole ring or pyrimidine ring, and the Ar₁ ring and/or the Ar₂ ring optionally have a group selected from an alkyl group having 1 to 10 carbon atoms, and an alkoxy group having 1 to 10 carbon atoms.

13. The aromatic compound according to claim 6, wherein the Ar₁ ring is a thiophene ring or pyrrole ring, the Ar₂ ring is a pyridine ring, pyrazole ring, oxazole ring, thiazole ring or pyrimidine ring, and the Ar₁ ring and/or the Ar₂ ring optionally have a group selected from an alkyl group having 1 to 10 carbon atoms, and an alkoxy group having 1 to 10 carbon atoms.

* * * * *